United States Patent [19]

Chou et al.

[11] Patent Number: 5,625,069
[45] Date of Patent: Apr. 29, 1997

[54] PROCESS FOR PREPARING 2-CYANO-3,5-DIMETHYL-4-METHOXYPYRIDINE

[75] Inventors: Shan-Yen Chou, Taipei; Tsai-Mien Huang, Changhua; Shyh-Fong Chen; Hao Ku, both of Taipei, all of Taiwan

[73] Assignee: Development Center for Biotechnology, China

[21] Appl. No.: 681,214

[22] Filed: Jul. 22, 1996

[51] Int. Cl.$^6$ .................................................. C07D 213/12
[52] U.S. Cl. ........................... 546/250; 546/288; 546/298; 549/420; 568/417
[58] Field of Search ............................... 546/250, 288, 546/298; 549/420; 568/417

[56] References Cited

U.S. PATENT DOCUMENTS

| 4,255,431 | 3/1981 | Junggren et al. | 424/263 |
| 5,066,810 | 11/1991 | Baumann | 546/300 |

OTHER PUBLICATIONS

March, J., Advanced Organic Chemistry: Reactions, Mechanisms, and Structure, 4th Ed., 1992, pp. 421–423 and 1041–1042.
Castellanos, M.L. et al, J. Chem. Soc. Perkin Trans. I, 1985, 6, pp. 1209–1215.
Xue, T. et al, Huaxue Xuebao, 1986, 44(11), pp. 1129–1133.

*Primary Examiner*—C. Warren Ivy
*Assistant Examiner*—Garth M. Dahlen
*Attorney, Agent, or Firm*—Fish & Richardson P.C.

[57] ABSTRACT

A process of preparing 2-cyano-3,5-dimethyl-4-methoxypyridine. The process includes the steps of: acylating 2-methyl-1-penten-1-alkoxy-3-one to obtain 2-alkoxycarbonyl-3,5-dimethyl-4-pyrone; ammonolyzing 2-alkoxycarbonyl-3,5-dimethyl-4-pyrone to obtain 2-carboxamido-3,5-dimethyl-4(1H)-pyridone; methylating 2-carboxamido-3,5-dimethyl-4(1H)-pyridone to obtain 2-carboxamido-3,5-dimethyl-4-methoxypyridine; and dehydrating said 2-carboxamido-3,5-dimethyl-4-methoxypyridone to obtain 2-cyano-3,5-dimethyl-4-methoxypyridine.

20 Claims, No Drawings

PROCESS FOR PREPARING 2-CYANO-3,5-DIMETHYL-4-METHOXYPYRIDINE

BACKGROUND OF THE INVENTION

Omeprazole (trade name Prilosec), a specific inhibitor of the gastric proton pump ($H^+ + K^+$)-ATPase, can be prepared by coupling 2-chloromethyl-3,5-dimethyl-4-methoxypyridine and 5-methoxy-2-mercaptobenzimidazole, followed by oxidation. 2-Chloromethyl-3,5-dimethyl-4-methoxypyridine is readily obtainable by chlorination of 2-hydroxymethyl-3,5-dimethyl-4-methoxypyridine, which, in turn, can be prepared from 2-cyano-3,5-dimethyl-4-methoxypyridine, i.e., compound 1 shown in Scheme A below, by procedures well known in the art (see, e.g., European Patent Application 369,208).

Conventional methods of preparing 2-hydroxymethyl-3,5-dimethyl-4-methoxypyridine involve using either N-oxide or nitropyridine as an intermediate. E.g., see U.S. Pat. No. 4,255,431 and European Patent Application 369,208. Both N-oxide and nitropyridine have been reported to be carcinogenic.

SUMMARY OF THE INVENTION

The present invention features a process of preparing 2-cyano-3,5-dimethyl-4-methoxypyridine. The process includes the following steps:

(1) acylating 2-methyl-1-penten-1-alkoxy-3-one to obtain 2-alkoxycarbonyl-3,5-dimethyl-4-pyrone (the alkoxy of 2-methyl-1-penten-1-alkoxy-3-one can contain one or more carbons, e.g., $C_{1-8}$ or $C_{1-12}$; examples include, but are not limited to, ethoxy, propoxy, iso-propoxy, butoxy, and benzyloxy);

(2) ammonolyzing 2-alkoxycarbonyl-3,5-dimethyl-4-pyrone to obtain 2-carboxamido-3,5-dimethyl-4(1H)-pyridone;

(3) methylating 2-carboxamido-3,5-dimethyl-4(1H)-pyridone to obtain 2-carboxamido-3,5-dimethyl-4-methoxypyridine; and (4) dehydrating 2-carboxamido-3,5-dimethyl-4-methoxypyridone to obtain 2-cyano-3,5-dimethyl-4-methoxypyridine.

More specifically, the acylating step can be effected by contacting 2-methyl-1-penten-1-alkoxy-3-one with dialkyloxalate (e.g., diethyloxalate) to obtain 2-alkoxycarbonyl-3,5-dimethyl-4-pyrone. Note that each of the two alkyl groups of dialkyloxalate, which are either the same or different, can contain one or more carbons, e.g. $C_{1-8}$ or $C_{1-12}$.

The ammonolyzing step, on the other hand, can be performed by contacting 2-alkoxycarbonyl-3,5-dimethyl-4-pyrone with an ammonolyzing agent (e.g., liquid ammonia, aqueous ammonia, ethanolic ammonia, and methanolic ammonia) to obtain 2-carboxamido-3,5-dimethyl-4(1H)-pyridone.

To perform the methylating step, one can react 2-carboxamido-3,5-dimethyl-4(1H)-pyridone with a methylating agent, such as dimethyl sulfate and methyl iodide, to obtain 2-carboxamido-3,5-dimethyl-4-methoxypyridine.

Dehydrating agents, such as $(CF_3CO)_2O$, $POCl_3$, and $SOCl_2$, can be used either singly or in combination, in the dehydrating step so as to convert 2-carboxamido-3,5-dimethyl-4-methoxypyridone to 2-cyano-3,5-dimethyl-4-methoxypyridine.

Other features or advantages of the present invention will be apparent from the following detailed description and also from the appending claims.

DETAILED DESCRIPTION OF THE INVENTION

Without further elaboration, it is believed that one skilled in the art can, based on the description herein, utilize the present invention to its fullest extent. The following specific examples are, therefore, to be construed as merely representative, and not limitative of the remainder of the disclosure in any way whatsoever. All publications cited in this disclosure are incorporated by reference.

Scheme A below is illustrative of the process of the invention:

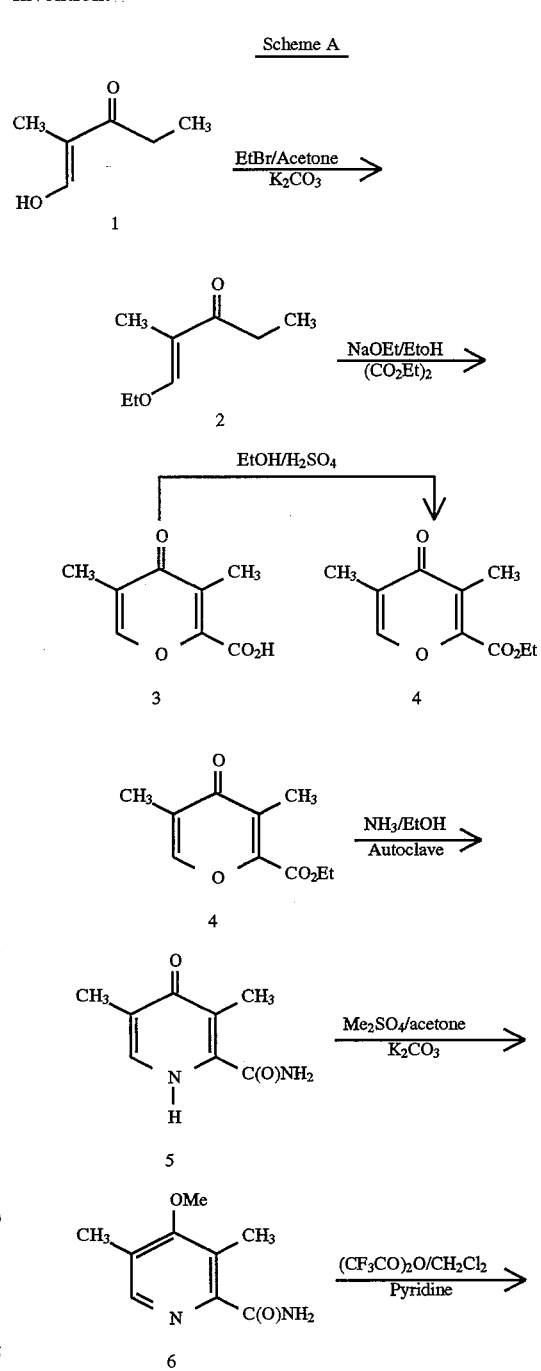

-continued
Scheme A

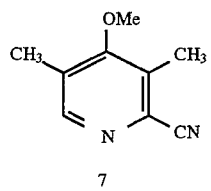

7

According to Scheme A, O-alkylated product, 2-methyl-1-penten-1-ethoxy-3-one 2 is prepared by alkylation of 2-methyl-1-penten-3-one-1-ol 1 with ethyl bromide in refluxing acetone. Alkyl bromides other than ethyl bromide can be used if other 2-methyl-1-penten-1-alkoxy-3-one compounds are to be prepared. Compound 2 is then subjected to acylation followed by concomitant ring-closure with diethyloxalate (or other dialkyloxalate) as the acylating agent, producing a mixture of 3 and 4. Compound 3 is a saponification product of 4 formed by the residual water present in commercial ethanol (0.2% max). Compound 3 can be converted to 4 by esterification. Compound 4 is then heated (e.g., in an autoclave) with an ammonolyzing agent such as ethanolic ammonia, giving pyridone amide 5. Methylation of compound 5 by a standard method (e.g., Me$_2$SO$_4$/acetone, K$_2$CO$_3$) leads to an O-methylated product 6. The O-methylated product 6 can then be treated with trifluroacetic anhydride and pyridine in a proper solvent such as CH$_2$Cl$_2$, giving 2-cyano-3, 5-dimethyl-4-methoxypyridine 7.

An example of the process depicted in scheme A is provided in detail below:

Preparation of 2-Methyl-1-Penten-1-Ethoxy-3-One 2

To a solution of 2-methyl-1-penten-3-one-1-ol 1 (76 g, 0.67 mol) in acetone (1.5 liter) was added ethyl bromide (209 g, 1.92 mol) and anhydrous potassium carbonate (115 g, 0.83 mol). The mixture was refluxed for 34 hr. After the solvent had been evaporated, the residue was treated with water and extracted twice with ether. The ether extract was washed with dilute potassium carbonate and water and dried over anhydrous magnesium sulfate. Evaporation of the ether under reduced pressure followed by vacuum distillation gave 2 (80.3 g, 84% yield) as a yellow oil.

$^1$H-NMR (CDCl$_3$) δ 7.33 (s, 1H), 4.08 (q, J=7.2HZ, 2H), 2.56 (q, J=7.4Hz, 2H), 1.73 (s, 3H), 1.36 (t, J=7.2HZ, 3H), 1.13 ( t, J=7.4Hz, 3H) .

Anal. Calcd for C$_8$H$_{14}$O$_2$: C, 67.50; H, 9.92. Found: C, 67.25; H, 9.87.

Preparation of 2-Carboxylic Acid-3,5-Dimethyl-4-Pyrone 3 and 2-ethoxycarbonyl-3,5-dimethyl-4-pyrone 4

To a refluxing solution of ethanolic sodium ethoxide solution (50 ml, 0.626 M) was added a mixture of compound 2 (4.05 g, 0.028 mol) and diethyl oxalate (4.1 g, 0.028 mol) over 0.5 hr. After another 0.5 hr the solvent was evaporated and the residue was poured into ice-water. The mixture was extracted with dichloromethane (100 ml×2) and washed with water. The organic layer was dried and removal of the solvent gave crude products, which was recrystallized from n-hexane to give compound 4 as a white powder (2.2 g, 40% yield), mp 81°–83° C.

$^1$H-NMR (CDCl$_3$) δ 7.73 (s, 1H), 4.42 (q, J=7.2Hz, 2H), 2.31 (s, 3H), 1.96 (s, 3H), 1.42 (t, J=7.2HZ, 3H).

Ms (13eV) m/z (%): 196.1 (M$^+$, 45), 167.1 (100).

Anal. Calcd for C$_{10}$H$_{12}$O$_4$: C, 61.22; H, 6.16. Found: C, 61.18; H, 6.12.

The aqueous solution and washings were combined and acidified with conc. HCl at 0° C. The resulting precipitate was filtered and dried in vacuo to give compound 3 as a white powder (0.94 g, 20% yield), mp 185°–187° C.

$^1$H-NMR (DMSO-d6) δ 8.19 (s, 1H), 2.15 (s, 3H), 1.83 (s, 3H).

Ms (13eV) m/z (%): 168.0 (M$^+$, 100), 124.1 (20), 95.0 (20).

Anal Calcd for C$_8$H$_8$O$_4$: C, 57.15; H, 4.80. Found: C, 57.10; H, 4.75.

Esterification of 2-Carboxylic Acid-3,5-Dimethyl-4-Pyrone 3 to 2-ethoxycarbonyl-3,5-dimethyl-4-pyrone 4

To a solution of compound 3 (3 g, 17.7 mmol) in abs. Ethanol (30 ml) was added sulfuric acid (0.5 g). The mixture was refluxed for 5 hr and then the solvent was evaporated. The residue was partitioned between chloroform and 10% potassium carbonate aqueous solution. The separated chloroform layer was washed with water, dried and evaporated to give compound 4 (3.2 g, 92% yield).

Preparation of 2-Carboxamide-3,5-Dimethyl-4(1H)-Pyridone 5

A solution of pyrone 4 (10.2 g, 52.0 mmol) in saturated ethanolic ammonia (180 ml) was heated at 120° C. in an autoclave for 48 hr. The mixture was cooled and filtered to give compound 5 (6.2 g) as a white powder. The filtrate was evaporated, and the residue was triturated with small amount of cold methanol to give compound 5 (1.7 g) as the second crop. The combined yield of compound 5 is 7.9 g (91%), mp>200° C.

$^1$H-NMR (DMSO-d$_6$) δ 8.02 (brs, 1H), 7.85 (brs, 1H), 7.59 (s, 1H), 2.01 (s, 3H), 1.91 (s, 3H).

Anal. Calcd for C$_8$H$_{10}$N$_2$O$_2$: C, 57.82; H, 6.07, N, 16.86. Found: C, 57.62, H, 6.03; N, 16.72.

Preparation of 2-Carboxamide-3,5-Dimethyl-4-Methoxypyridine 6

A mixture of compound 5 (1.6 g, 9.6 mmol), dimethyl sulfate (1.2 g, 9.52 mmol), and anhydrous potassium carbonate (4.1 g, 29.7 mmol) in acetone (50 ml) was heated under reflux for 15 hr. It was then filtered and washed with acetone. The filtrate was evaporated, and the residue was partitioned between ethyl acetate and water. The organic layer was washed with water, dried and evaporated to give compound 6 (1.55 g, 90% yield) as a white powder mp 127°–129° C.

$^1$H-NMR (CDCl$_3$) 8.20 (s, 1H), 7.83 (brs, 1H), 5.56 (brs, 1H), 3.78 (s, 3H), 2.64 (s, 3H), 2.31 (s, 3H).

Ms(13eV) m/z(%): 180.1 (M$^+$, 100), 163.1(100), 135.1 (75) , 105.1(60).

Anal. Calcd for C$_9$H$_{12}$N$_2$O$_2$: C, 59.99; H, 6.71; N, 15.55. Found: C, 59.87; H, 6.56; N, 15.32.

Preparation of 2-Cyano-3,5-Dimethyl-4-Methoxypyridine

To a suspension of amide 6 (0.8 g, 4.44 mmol) in dry dichloromethane (20 ml) was added pyridine (0.71 g, 8.99mmol) followed by trifluoroacetic anhydride (1.12 g, 5.33 mmol). The internal temperature was maintained <30°

C. The mixture was stirred at room temperature overnight. It was washed with water, dried and evaporate to give 7 (0.65 g, 91% yield). It showed same analytic data as those of an authentic sample.

Other Embodiments

From the above description, one skilled in the art can easily ascertain the essential characteristics of the present invention, and, without departing from the spirit and scope thereof, can make various changes and modifications of the invention to adapt it to various usages and conditions. For example, a process similar to that described above can be used to prepare analogs of 2-cyano-3,5-dimethyl-4-methoxypyridine, such as 2-cyano-3,5-dimethyl-4-ethoxypyridine. Thus, other embodiments are also within the claims.

What is claimed is:

1. A process of preparing 2-cyano-3,5-dimethyl-4-methoxypyridine, comprising the following steps:

acylating 2-methyl-1-penten-1-alkoxy-3-one to obtain 2-alkoxycarbonyl-3,5-dimethyl-4-pyrone;

ammonolyzing said 2-alkoxycarbonyl-3,5-dimethyl-4-pyrone to obtain 2-carboxamido-3,5-dimethyl-4(1H)-pyridone;

methylating said 2-carboxamido-3,5-dimethyl-4(1H)-pyridone to obtain 2-carboxamido-3,5-dimethyl-4-methoxypyridine; and dehydrating said 2-carboxamido-3,5-dimethyl-4-methoxypyridone to obtain 2-cyano-3,5-dimethyl-4-methoxypyridine.

2. The process of claim 1, wherein the alkoxy of said 2-methyl-1-penten-1-alkoxy-3-one contains 1–8 carbons.

3. The process of claim 2, wherein said acylating step comprises contacting said 2-methyl-1-penten-1-alkoxy-3-one with dialkyloxalate to obtain said 2-alkoxycarbonyl-3,5-dimethyl-4-pyrone, wherein each of the two alkyl groups of said dialkyloxalate, which can be the same or different, contains 1–8 carbons.

4. The process of claim 3, wherein said dialkyloxalate is diethyloxalate.

5. The process of claim 3, wherein said alkoxy is selected from the group consisting of ethoxy, propoxy, isopropoxy, butoxy, and benzyloxy.

6. The process of claim 5, wherein said ammonolyzing step comprises contacting said 2-alkoxycarbonyl-3,5-dimethyl-4-pyrone with an ammonolysis agent selected from the group consisting of liquid ammonia, aqueous ammonia, ethanolic ammonia, and methanolic ammonia to obtain said 2-carboxamido-3,5-dimethyl-4(1H)-pyridone; said methylating step comprises contacting said 2-carboxamido-3,5-dimethyl-4(1H)-pyridone with a methylation agent selected from the group consisting of dimethyl sulfate and methyl iodide to obtain said 2-carboxamido-3,5-dimethyl-4-methoxypyridine; and said dehydrating step comprises contacting said 2-carboxamido-3,5-dimethyl-4-methoxypyridone with a dehydration agent selected from the group consisting of $(CF_3CO)_2O$, $POCl_3$, and $SOCl_2$ to obtain said 2-cyano-3,5-dimethyl-4-methoxypyridine.

7. The process of claim 5, wherein said alkoxy is selected from the group consisting of ethoxy, propoxy, isopropoxy, butoxy, and benzyloxy.

8. The process of claim 7, wherein said dialkyloxalate is diethyloxalate.

9. The process of claim 2, wherein said ammonolyzing step comprises contacting said 2-alkoxycarbonyl-3,5-dimethyl-4-pyrone with an ammonolysis agent selected from the group consisting of liquid ammonia, aqueous ammonia, ethanolic ammonia, and methanolic ammonia to obtain said 2-carboxamido-3,5-dimethyl-4(1H)-pyridone.

10. The process of claim 9, wherein said alkoxy is selected from the group consisting of ethoxy, propoxy, isopropoxy, butoxy, and benzyloxy.

11. The process of claim 2, wherein said methylating step comprises contacting said 2-carboxamido-3,5-dimethyl-4(1H)-pyridone with a methylation agent selected from the group consisting of dimethyl sulfate and methyl iodide to obtain said 2-carboxamido-3,5-dimethyl-4-methoxypyridine.

12. The process of claim 11, wherein said alkoxy is selected from the group consisting of ethoxy, propoxy, isopropoxy, butoxy, and benzyloxy.

13. The process of claim 2, wherein said dehydrating step comprises contacting said 2-carboxamido-3,5-dimethyl-4-methoxypyridone with a dehydration agent selected from the group consisting of $(CF_3CO)_2O$, $POCl_3$, and $SOCl_2$ to obtain said 2-cyano-3,5-dimethyl-4-methoxypyridine.

14. The process of claim 13, wherein said alkoxy is selected from the group consisting of ethoxy, propoxy, isopropoxy, butoxy, and benzyloxy.

15. The process of claim 2, wherein said alkoxy is selected from the group consisting of ethoxy, propoxy, isopropoxy, butoxy, and benzyloxy.

16. The process of claim 1, wherein said acylating step comprises contacting said 2-methyl-1-penten-1-alkoxy-3-one with dialkyloxalate to obtain said 2-alkoxycarbonyl-3,5-dimethyl-4-pyrone, wherein each of the two alkyl groups of said dialkyloxalate, which can be the same or different, contains 1–8 carbons.

17. The process of claim 16, wherein said dialkyloxalate is diethyloxalate.

18. The process of claim 16, wherein said ammonolyzing step comprises contacting said 2-alkoxycarbonyl-3,5-dimethyl-4-pyrone with an ammonolysis agent selected from the group consisting of liquid ammonia, aqueous ammonia, ethanolic ammonia, and methanolic ammonia to obtain said 2-carboxamido-3,5-dimethyl-4(1H)-pyridone.

19. The process of claim 16, wherein said methylating step comprises contacting said 2-carboxamido-3,5-dimethyl-4(1H)-pyridone with a methylation agent selected from the group consisting of dimethyl sulfate and methyl iodide to obtain said 2-carboxamido-3,5-dimethyl-4-methoxypyridine.

20. The process of claim 16, wherein said dehydrating step comprises contacting said 2-carboxamido-3,5-dimethyl-4-methoxypyridone with a dehydration agent selected from the group consisting of $(CF_3CO)_2O$, $POCl_3$, and $SOCl_2$ to obtain said 2-cyano-3,5-dimethyl-4-methoxypyridine.

* * * * *